United States Patent
Young et al.

(10) Patent No.: US 12,053,773 B2
(45) Date of Patent: Aug. 6, 2024

(54) DEVICE FOR ENUMERATING MICROORGANISMS

(71) Applicant: 3M INNOVATIVE PROPERTIES COMPANY, St. Paul, MN (US)

(72) Inventors: Alexi J. Young, Shoreview, MN (US); John M. Kruse, Minneapolis, MN (US); Christopher M. Brown, Cottage Grove, MN (US); Donald G. Peterson, Shoreview, MN (US); Evan D. Brutinel, Inver Grove Heights, MN (US)

( * ) Notice: Subject to any disclaimer, the term of this patent is extended or adjusted under 35 U.S.C. 154(b) by 769 days.

(21) Appl. No.: 17/056,884

(22) PCT Filed: May 23, 2019

(86) PCT No.: PCT/IB2019/054305
§ 371 (c)(1),
(2) Date: Nov. 19, 2020

(87) PCT Pub. No.: WO2019/229600
PCT Pub. Date: Dec. 5, 2019

(65) Prior Publication Data
US 2021/0114017 A1    Apr. 22, 2021

Related U.S. Application Data

(60) Provisional application No. 62/677,220, filed on May 29, 2018.

(51) Int. Cl.
*B01L 3/00* (2006.01)
*B01L 99/00* (2010.01)
*C12Q 1/04* (2006.01)

(52) U.S. Cl.
CPC .............. *B01L 3/5023* (2013.01); *B01L 3/505* (2013.01); *C12Q 1/04* (2013.01); *B01L 2300/0887* (2013.01); *B01L 2300/123* (2013.01)

(58) Field of Classification Search
CPC ........... B01L 2300/0887; B01L 3/5023; B01L 3/505; B01D 1/221
See application file for complete search history.

(56) References Cited

U.S. PATENT DOCUMENTS

| | | |
|---|---|---|
| 3,929,583 A | 12/1975 | Sharpe |
| 4,485,171 A | 11/1984 | Ikeda |

(Continued)

FOREIGN PATENT DOCUMENTS

| | | |
|---|---|---|
| CA | 2176895 | 8/1999 |
| EP | 0368541 | 5/1990 |

(Continued)

OTHER PUBLICATIONS

International Search Report for PCT International Application No. PCT/IB2019/054305, mailed on Aug. 29, 2019, 5 pages.

*Primary Examiner* — Lydia Edwards
(74) *Attorney, Agent, or Firm* — HYLTON-RODIC LAW PLLC

(57) ABSTRACT

A microbial detection device and methods of use are provided. The device comprises a water-proof pouch that includes a first wall portion, a second wall portion, and a porous membrane filter disposed in the pouch between the first and second wall portions. The filter membrane divides the pouch into first and second compartments. A dry, cold water-soluble gelling agent is adhered to the pouch in the first compartment and an absorbent pad is disposed in the second compartment. A release liner removably adhered to the first adhesive layer.

18 Claims, 4 Drawing Sheets

(56) References Cited

U.S. PATENT DOCUMENTS

| | | | |
|---|---|---|---|
| 4,565,783 | A | 1/1986 | Hansen |
| 5,089,413 | A | 2/1992 | Nelson |
| 5,232,838 | A | 8/1993 | Nelson |
| 5,409,838 | A | 4/1995 | Wickert |
| 5,770,086 | A | 6/1998 | Indriksons |
| 6,977,323 | B1 * | 12/2005 | Swenson ............... A61L 15/425 602/41 |
| 2013/0344488 | A1 | 12/2013 | Mach |
| 2016/0042712 | A1 | 2/2016 | Su |

FOREIGN PATENT DOCUMENTS

| | | |
|---|---|---|
| JP | H05-013200 | 2/1993 |
| JP | H07-075545 | 3/1995 |
| JP | 2007-124985 | 5/2007 |
| WO | WO 2000-004348 | 1/2000 |
| WO | WO 2001-059060 | 8/2001 |
| WO | WO 2001-060422 | 8/2001 |
| WO | WO 2005-058453 | 6/2005 |
| WO | WO 2014-054494 | 4/2014 |
| WO | WO 2017-019345 | 2/2017 |
| WO | WO 2018-125811 | 7/2018 |

\* cited by examiner

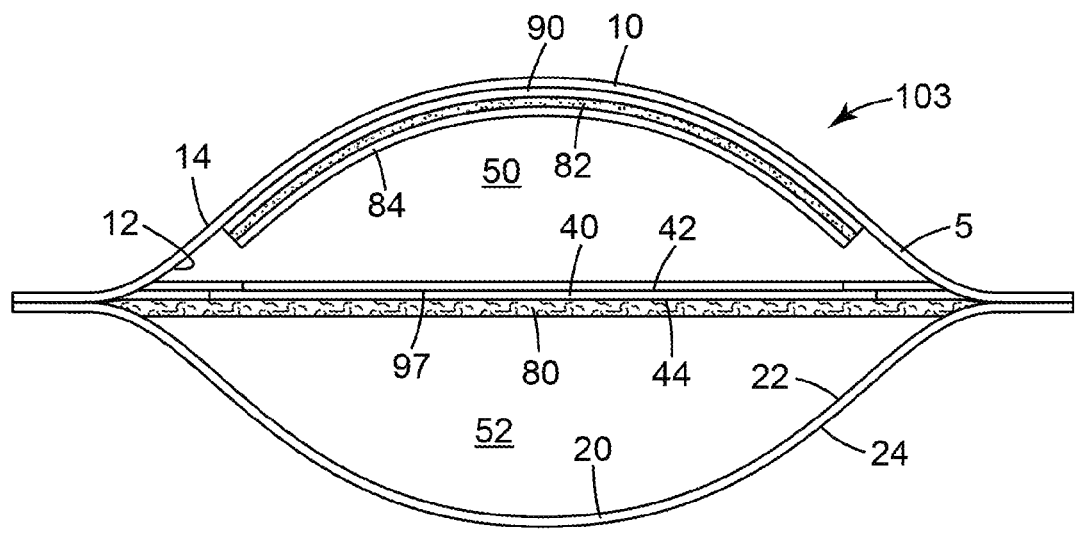
*Fig. 1*
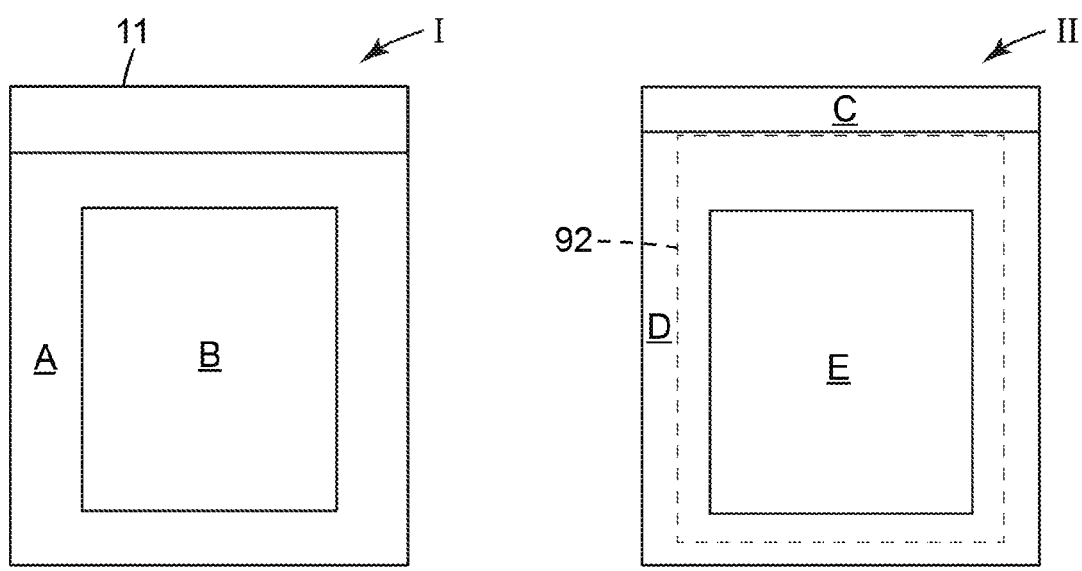
*Fig. 2A*  *Fig. 2B*

DEVICE FOR ENUMERATING MICROORGANISMS

BACKGROUND

Many industries need to detect and quantify biological material in a sample, for instance, the determination of microbial concentration in food and water is an essential part of food and water quality testing. Similar demands arise from a multitude of industries including food, biotechnological, pharmaceutical, water treating industry, and also in medical microbiological diagnostics, environmental and scientific research. Samples are commonly scrutinized to, for instance, monitor microbial population in a production environment, in-process controls, post storage and also final product testing.

Classical methods for the examination of samples particularly liquid samples typically demands incubation time or reaction time for analysis. Analysis may involve several different kinds of chemical, biochemical, physical or optical techniques and require many hours or even days for incubation and subsequent analysis. Reducing the time and/or labor for quantitative and qualitative analysis of samples is essential for making rapid decisions in quality and process control operations.

With regard to testing of aqueous biological samples, it is advantageous to test large-volume samples, in order to detect relatively low concentrations of certain microorganisms (e.g., pathogenic microorganisms). Large-volume samples are often concentrated by filtration or centrifugation, for example, in order to make the sample more amenable to the traditional detection techniques (e.g., culture detection, molecular genetic detection, and immunological detection).

Even though a variety of methods and devices exist for testing relatively large volumes of aqueous samples, there exists a need for improved devices.

SUMMARY

The present disclosure generally relates to a device for culturing and detecting microorganisms. In addition, the present disclosure relates to a method for culturing and detecting microorganisms in a sample. In particular, the present disclosure relates to detecting culturing and detecting microorganisms present in a relatively large sample volume in a self-contained thin-film culture device. The present disclosure provides devices and methods for detecting and/or enumerating target microorganisms in relatively-large (e.g., about 25 mL to about 150 mL) liquid samples. It is now known that a self-contained device can include all of the components needed to concentrate microorganisms from a large liquid sample, immobilize the microorganisms in a cold water-soluble gelling agent, and provide a moist nutrient environment sufficient to grow and detect colonies of the microorganisms. Advantageously, the device can be used to detect and/or enumerate a wide variety of microorganisms (e.g., bacteria, yeast, and filamentous fungi) present in a liquid sample.

In one aspect, the present disclosure provides a device for detecting microorganisms. The device can comprise a waterproof pouch. The waterproof pouch can comprise a first wall portion having an inner surface and an outer surface; a second wall portion having an inner surface and an outer surface; a porous membrane filter disposed in the pouch between the inner surface of the first wall portion and the inner surface of the second wall portion, the membrane filter having a first major surface and a second major surface opposite the first major surface; a frame coupled to the membrane filter, the frame having a first major surface and a second major surface opposite the first major surface; a first compartment defined in part by inner surface of the first wall portion and defined in part by the first major surface of the membrane filter; and a second compartment defined in part by the inner surface of the second wall portion and defined in part by the second major surface of the membrane filter; a dry cold water-soluble gelling agent adhered to the pouch in the first compartment; and an absorbent pad disposed in the second compartment. The membrane filter can permit passage of aqueous liquids from the first compartment to the second compartment and can prevent passage of particles of a predetermined size from the first compartment to the second compartment. In any embodiment, the frame is coated on the first major surface with a first adhesive layer and on the second major surface with a second adhesive layer and the frame comprises an aperture through which liquid passes from the first compartment into the membrane filter. The device further can comprise a release liner removably adhered to the first adhesive layer.

In another aspect, the present disclosure provides a method. The method can comprise placing a predetermined volume of aqueous sample into the first compartment of the device of any one of the above embodiments of the device, removing the release liner, sealing the device, incubating the device for a period of time at a temperature that facilitates growth and detection of a target microorganism, and detecting a presence or an absence of a colony of the target microorganism in the device.

As used herein, "reconstituted medium" refers to a solution or gel formed from the reconstitution of a cold-water-soluble powder with an aqueous liquid.

The term "cold-water-soluble powder", as used herein, refers to a powder that forms a gel in room temperature water (e.g., about 18° C. to 24° C.) when combined with an aqueous test sample.

The term "substantially impermeable to microorganisms and water vapor", as used herein, refers to a cover sheet that prevents undesired contamination and hydration of underlying layers of cold-water-soluble powder during shipping, storage, and use of thin film culture device(s), and avoids desiccation of the reconstituted medium, such that the reconstituted medium is suitable to support the growth of microorganisms during an incubation period.

The term "substantially water-free", as used herein, designates a water content no greater than about the water content of the ambient environment.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

As used herein, "a," "an," "the," "at least one," and "one or more" are used interchangeably. Thus, for example, a culture device comprising "an" indicator agent can be interpreted to mean that the culture device can comprise "one or more" indicator agents.

The term "and/or" means one or all of the listed elements or a combination of any two or more of the listed elements.

Also herein, the recitations of numerical ranges by endpoints include all numbers subsumed within that range (e.g., 1 to 5 includes 1, 1.5, 2, 2.75, 3, 3.80, 4, 5, etc.).

The features and advantages of the present invention will be understood upon consideration of the detailed description of the preferred embodiment as well as the appended claims. These and other features and advantages of the invention may be described below in connection with various illustrative embodiments of the invention.

The above summary of the present invention is not intended to describe each disclosed embodiment or every implementation of the present invention. The figures and the detailed description which follow more particularly exemplify illustrative embodiments. Other features, objects and advantages will become apparent from the description and drawings, and from the claims.

BRIEF DESCRIPTION OF DRAWINGS

FIG. 1 is a cross-sectional view of one embodiment of a device according to the present disclosure.

FIG. 2A is a first subassembly of the device of FIG. 2.

FIG. 2B is a second subassembly of the device of FIG. 2.

DETAILED DESCRIPTION

Figure 2:
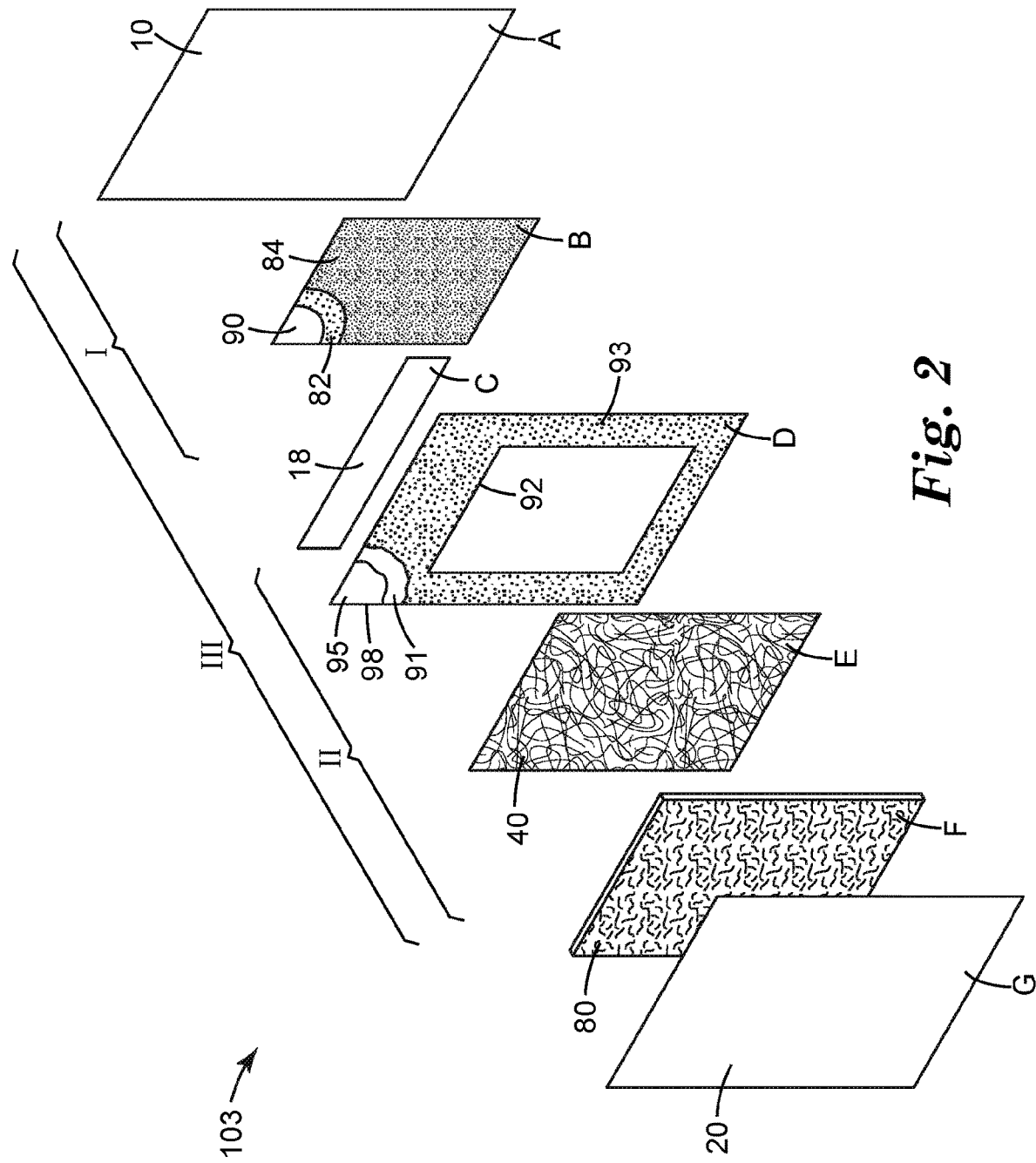
FIG. 2 is an exploded view of one embodiment of the device.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "connected" and "coupled" and variations thereof are used broadly and encompass both direct and indirect connections and couplings. Further, "connected" and "coupled" are not restricted to physical or mechanical connections or couplings. It is to be understood that other embodiments may be utilized and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure provides devices and methods for detecting and/or enumerating target microorganisms in relatively-large (e.g., about 25 mL to about 150 mL) liquid samples. It is now known that a self-contained device can include all of the components needed to concentrate microorganisms from a liquid sample, immobilize the microorganisms in a matrix, and provide a moist nutrient environment sufficient to grow and detect colonies of the microorganisms. Advantageously, the device can be used to detect and/or enumerate a wide variety of microorganisms (e.g., bacteria, yeast, and filamentous fungi) present in a liquid sample. In addition, the self-contained device provides certain advantages of thin-film culture devices such as, for example, sample-ready (i.e., just add liquid sample and then incubate), ease of use, portability, compactness, and a relatively long shelf-life.

A device of the present disclosure can be used to enumerate microorganisms in a sample of water (e.g., surface water, process water, potable water). The water can be interrogated for the presence of certain target microorganisms including, for example, coliforms, fecal coliforms, *E. coli*, and/or total aerobic count or aerobic plate count (APC), yeast and mold. The presence of fecal coliforms in a water sample can indicate contamination of the water with human fecal material, which may contain certain pathogenic bacteria and/or viruses.

The present disclosure provides a microbial detection device. FIGS. 1-4 show various views of one embodiment of a device 103 according to the present disclosure. In any embodiment, a device of the present disclosure can be partially assembled into one or more subassembly, which is subsequently combined with other components to make the device.

The device 103 comprises a waterproof pouch 5 defined by at least one wall. The at least one wall comprises a first wall portion 10 and a second wall portion 20. The first wall portion 10 has an inner surface 12 and an outer surface 14. The second wall portion 20 has an inner surface 22 and an outer surface 24. Disposed in the pouch 5 between the inner surface 12 of the first wall portion 10 and the inner surface 22 of the second wall portion 20 is a membrane filter 40. The membrane filter has a first major surface 42 and a second major surface 44 opposite the first major surface.

The pouch 5 is divided into at least two compartments (first compartment 50 and second compartment 52, respectively). The first compartment 50 is defined in part by the inner surface 12 of the first wall portion 10 and also defined in part by the first major surface 42 of the membrane filter 40. The second compartment 52 is defined in part by the inner surface 22 of the second wall portion 20 and defined in part by the second major surface 44 of the membrane filter 40.

The pouch 5 further comprises a dry (i.e., substantially water-free) cold water-soluble gelling agent 84 in the first compartment 50. In any embodiment, the dry coating 84 may be adhered to a first substrate 90 (e.g., adhered to an adhesive layer 82 coated on the substrate) that is adhered to the first wall portion 10 of the pouch 5. In addition, the pouch 5 has an absorbent pad 80 disposed in the second compartment 52. The area defined by the coating comprising the cold-water-soluble gelling agent also defines the area in which microorganisms from the sample grow and are enumerated after a sample is deposited into the first compartment. Because the device comprises an absorbent pad (described below) that absorbs most of the liquid from the sample, the cold-water-soluble gelling agent is hydrated by only a fraction of the liquid sample. Advantageously, the devices of the present disclosure use a surprisingly smaller ratio of growth area: sample volume than previously-reported thin-film culture devices.

Referring to FIG. 2, an exploded view of one embodiment of the device, the device 103 can include a first subassembly I that comprises a first part A and a second part B. The first part A consists of the first wall portion 10. second part B includes a first substrate 90 coated on one side with an adhesive layer 82. Disposed on the adhesive layer 82 is a coating 84 that comprises the dry, cold water-soluble gelling agent described herein. The coating 84 can be deposited onto the adhesive layer 82 as a dry powder or as a liquid composition that is subsequently dried to a substantially water-free state, as described hereinabove. The first substrate 90 can comprise a sheet-like material similar to those used for the walls of the pouch as described above. Alternatively, the first substrate can comprise a nonwoven fabric or a cellulosic material (e.g., paper). In any embodiment, the cellulosic material can be coated with a waterproof coating that is substantially noninhibitory to growth of microorganisms. The area defined by the coating 84 on second part B also defines the growth and colony-enumeration area in the assembled device. In addition, the second part B can be positioned centrally over part A with the coating 84 facing away from the first wall portion 10. Another view of the assembled first subassembly I is shown in FIG. 2A.

Referring back to FIG. 2, a second subassembly II includes a third part C, a fourth part D and a fifth part E. Third part C can include a release liner 18 as described herein. The fourth part D comprises a second substrate 91. The second substrate 91 forms a frame comprising an aperture 92. The second substrate 91 has a first major surface and a second major surface opposite the first major surface. The second substrate 91 is coated on the first major surface with a first adhesive layer 93 and on the second major surface with a second adhesive layer 95. Alternatively, the second substrate 91 can be only coated with one adhesive layer 93. The second substrate 91 can comprise a sheet-like material (e.g., a flexible film) similar to those used for the walls of the pouch as described above. Alternatively, the second substrate can comprise a nonwoven fabric or a cellulosic material (e.g., paper). In any embodiment, the cellulosic material can be coated with a waterproof coating that is substantially noninhibitory to growth of microorganisms. Optionally, the absorbent pad can be coupled to the second substrate in the second compartment. When assembling subassembly II, the release liner 18 can be releasably adhered to the first adhesive layer 95 along the edge (edge 98).

Figure 3:
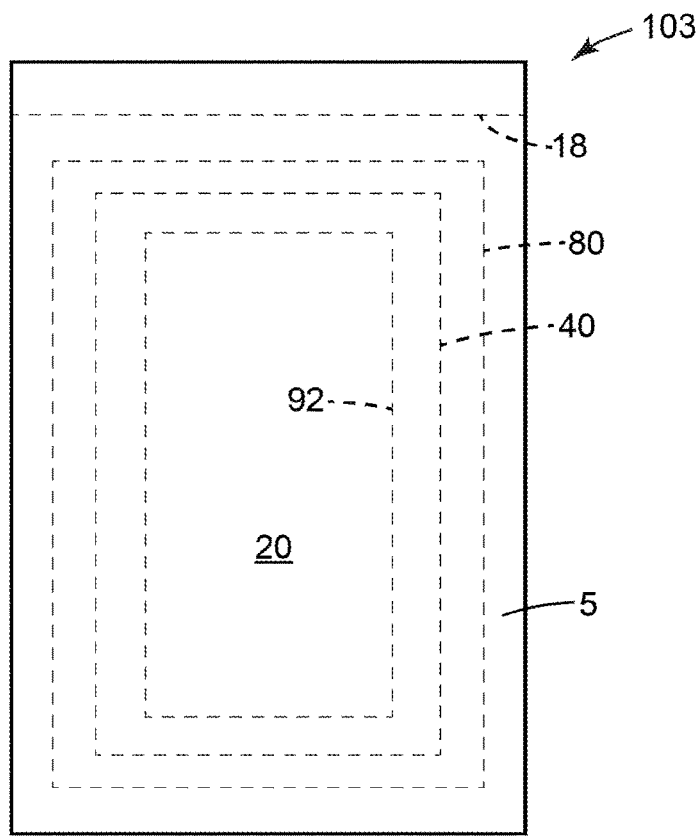
FIG. 3 is a plan view of the assembled device of FIG. 2.

The second subassembly II also includes the fifth part E (i.e., membrane filter 40, as described herein). The membrane filter 40 is dimensioned so that it completely covers the area defined by the aperture 92. When assembling subassembly II, the membrane filter 40 is adhered to the second adhesive layer 93 so that it completely covers the aperture 92 of the second substrate 91, as shown in FIG. 3. In use, liquid passes through the aperture from the first compartment to the second compartment of the device as the liquid passes through the membrane filter. In any embodiment, the aperture 92 defines a first area and the coating 84 defines a second area. Preferably, the second area is greater than or equal to the first area. More preferably, the second area is shaped and dimensioned to completely overlap the area of the aperture.

Optionally, when assembling the device 103 of FIG. 2, the subassembly I can be coupled to subassembly II to form a subassembly III. This can be done by placing the back side (i.e., the side that includes adhesive layer 95) of subassembly II in overlaying contact with the first wall portion 10 of subassembly I. In addition, the aperture 92 of subassembly II is aligned with subassembly I so that it overlaps the second part B of subassembly I.

To complete the construction of the device 103, the sixth part F (i.e., absorbent pad 80, as described herein) is placed in overlaying contact with the membrane filter 40 of the subassembly III and the seventh part (i.e., second wall portion 20, as described herein) is placed in overlaying contact with the first part A such that the seventh part G is adhesively coupled to the portion of the second adhesive layer 93 at the periphery of the part D. FIG. 3 shows a plan view of the assembled device 103 of FIG. 2.

Figure 4:
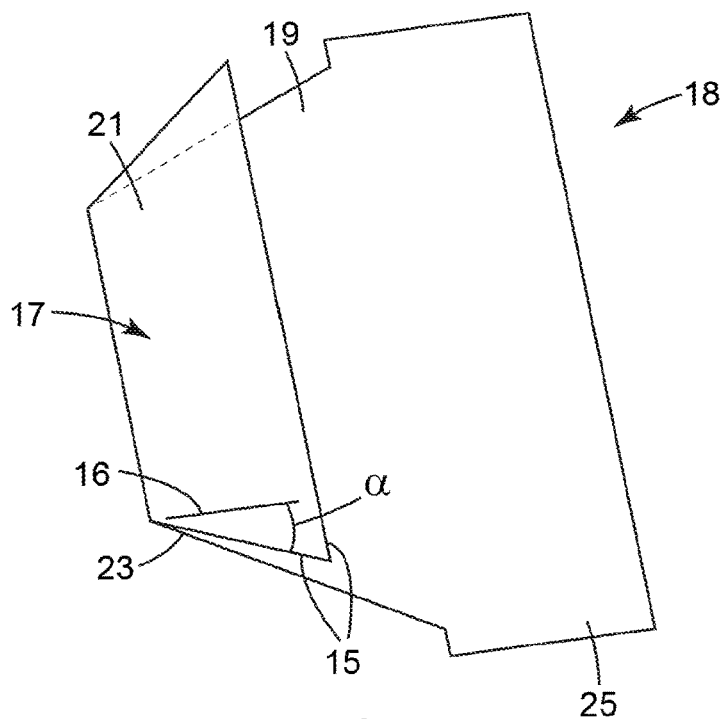
FIG. 4 is a perspective view of one embodiment of a release liner.

In some embodiments, the release liner 18 can be a J fold type release liner. Referring to FIG. 4, a perspective view of one embodiment of J fold type release liner, the release liner 18 comprises a edge 15 and at least a portion of the edge 15 has a slope that is oriented at an effective angle $\alpha$ with respect to the longitudinal axis 16 of the release liner. Effective angle $\alpha$ can be between 10 degrees and 80 degrees, between 20 degrees and 70 degrees, between 30 degrees and 60 degrees, between 40 degrees and 50 degrees. In some embodiments, effective angle $\alpha$ can be about 45 degrees. The release liner 18 can have a first major surface 17 and a second major surface 19. In some embodiments, a first portion 21 of the first major surface 17 of the release liner can face the first wall portion 10 and a second portion 23 of the first major surface 17 of the release liner can adhere to the first adhesive layer 95. The release liner 18 can have a tab 25 for removal of the release liner from the microbial detection device and the pouch 5 can be sealed.

In contrast to previous thin-film culture devices, a device of the present disclosure is configured to receive 100-150 mL of a liquid sample and has a growth area (that includes a cold water-soluble gelling agent) of about 80 $cm^2$. Thus, the microorganisms from the 150 mL sample volume is spread over a growth area that is equivalent to less than 1 $cm^2$ per mL of sample.

The pouch 5 (i.e., at least one wall, and wall portions thereof) is fabricated of a water-proof, deformable material. In any embodiment, the deformable material may comprise a flexible, sheet-like material such as a polymeric film, for example. Suitable materials for use when fabricating the at least one wall include polyethylene, polypropylene, polyethylene terephthalate, polyamide, polyurethane, polyvinyl chloride, polyacrylate, polyurea, and combinations thereof. The at least one wall of the pouch can be relatively thin (e.g., approximately 25 microns thick) or relatively thicker (e.g., approximately 125 microns thick), provided at least a portion of the at least one wall (e.g., first wall portion 10, which is opposite the membrane filter 40 in the first compartment 50) can deform when the pouch 5 receives a liquid sample (not shown) and/or at least a portion of the at least one wall (e.g., second wall portion 20, which is proximate the absorbent pad described herein) can deform when at least a portion of the sample passes from the first compartment into the second compartment.

The membrane filter 40 permits passage of a liquid (an aqueous liquid, not shown) from the first compartment 50 to the second compartment 52 and prevents passage of particles of a predetermined size from the first compartment to the second compartment. Thus, when an aqueous liquid sample suspected of containing a target microorganism is placed into the first compartment 50, a first portion of the aqueous liquid passes (e.g., by gravity flow) through the membrane filter 40 into the second compartment 52 where it is absorbed by the absorbent pad 80. The target microorganism is trapped on or in the filter membrane 40 or is retained in a second portion of the aqueous liquid that remains in the first compartment 50.

The use of membrane filters to trap and retain microorganisms is well known in the art. Accordingly, there are a number of suitable membrane filters that can be used in a device according to the present disclosure. Nonlimiting examples of suitable membrane filters include fibrous membrane filters made of nylon, polyether sulfone, polytetrafluoroethylene, or cellulosic materials (e.g., mixed cellulose esters), microporous plastic films (e.g., laser-etched polycarbonate film), and ceramic membrane filters.

The porosity of the membrane filter generally is chosen so that the target microorganisms will not pass all the way though the pores from one side of the membrane filter to the other side, thereby insuring that substantially all target microorganisms in the sample are retained by the filter. Typical bacteria are about 0.5 to 5.0 µm in length. Certain smaller bacteria, such as *Mycoplasma* spp., are approximately 0.3 µm in diameter. Yeast cells are generally larger than bacteria. Typical yeast cells are approximately 3-4 µm in diameter, although some are as large as about 40 µm in diameter. Molds may exist as single cells, spores, or filamentous hyphae. Although typically larger than bacteria, the average size of mold cells varies by species. Accordingly, the selection of a membrane filter with a suitable pore size may depend upon the target microorganism. For example, a membrane filter with a nominal pore size of 1.0 µm or less, 0.8 µm or less, 0.6 µm or less, 0.4 µm or less, 0.2 µm or less, 0.1 µm or less, 0.05 µm or less, 0.03 µm or less, 0.02 µm or less, or 0.01 µm or less may be suitable to capture and detect target bacteria. For capturing and detecting target yeast or mold microorganisms, a membrane filter with a nominal pore size of 12 µm or less, 8 µm or less, 5 µm or less, 3 µm or less, 2 µm or less, 1 µm or less, 0.8 µm or less, 0.6 µm or less, 0.4 µm or less, 0.2 µm or less, or 0.1 µm or less may be suitable.

Membrane filters may be prepared manually from suitable filtration media or, alternatively, may be purchased in pre-cut sizes and shapes. The size and shape of the membrane filter can be chosen based upon the sample volume and the expected load of particulate material in the sample. In general, membrane filters with larger surface areas will allow for higher filtration rates than membrane filters with smaller surface areas. Membrane filters may be used in combination with other filtration media (e.g., a prefilter, to trap larger debris in the sample) or other membrane filters.

In any embodiment, the membrane filter may be supported (e.g., by a scrim, not shown) to provide physical stability for the membrane during use. In any embodiment, the support may be attached to the membrane filter (e.g., on the second major surface). In any embodiment, the membrane filter can comprise a wetting agent (e.g., a nonionic surfactant) to facilitate rapid and complete penetration of the liquid sample throughout the membrane filters. Preferably, the wetting agent is in an amount sufficient to facilitate wetting the membrane with an aqueous liquid, but in an amount that does not substantially inhibit growth of the target microorganism when using the device.

The dry, cold water-soluble gelling agent is hydrated and forms a hydrogel when an aqueous sample is placed into the first compartment 50 of the pouch 5. As the first portion of the aqueous liquid moves through the membrane filter 40 from the first compartment 50 to the second compartment 52, the hydrogel contacts the first surface of the membrane filter 40, thereby immobilizing any microorganisms retained on or in the membrane filter.

Cold water-soluble gelling agents that are suitable for use in thin-film culture devices are known in the art and include, for example, cold-water-soluble natural and synthetic gelling agents. Natural gelling agents such as algin, carboxymethyl cellulose, tara gum, hydroxyethyl cellulose, guar gum, locust bean gum, xanthan gum, and synthetic gelling agents such as polyacrylamide, polyurethane, polyethylene oxides, and mixtures thereof are generally suitable. Appropriate gelling agents can be selected according to the teaching of this disclosure and the disclosures of U.S. Pat. Nos. 4,565,783; 5,089,413; and 5,232,838. Other preferred gelling agents include hydroxypropyl methylcellulose; these gelling agents being useful individually, or preferably, in combination with another gelling agent such as one of the aforementioned gelling agents.

In any embodiment, the dry, cold-water soluble gelling agent can be disposed in the pouch as a dry powder adhered to an adhesive layer, as described herein. Processes and adhesives for coating a dry powder onto a flexible film for use in a thin-film culture device are described, for example, in U.S. Pat. Nos. 4,565,783; 5,089,413; and 5,232,838. In any embodiment, the adhesive layer, if present may comprise an indicator for indicating microorganism growth. For example, the adhesive may comprise triphenyltetrazolium chloride as described in U.S. Pat. No. 5,409,838, which is incorporated herein by reference in its entirety.

In any embodiment, a device of the present disclosure optionally may comprise an effective amount of one or more dry nutrient (e.g., a nutrient medium selected to support growth of the target microorganism). The one or more dry nutrient may be disposed in the first compartment, for example. In any embodiment, the one or more dry nutrient may be disposed in the device (e.g., in the first compartment) as a dry powder or agglomerated powder. In any embodiment, the one or more nutrient can be adhered to the pouch (e.g., adhered to the first wall portion in the first compartment). In any embodiment, the one or more nutrient may be adhered to an adhesive layer that is adhered to the first wall portion, as described herein for the dry, cold water-soluble gelling agent.

In any embodiment, the dry cold water-soluble gelling agent can be deposited onto the first wall portion of the pouch as an aqueous composition, optionally comprising the one or more nutrient, and subsequently dried, as described in U.S. Pat. Nos. 4,565,783; 5,089,413; and 5,232,838. Before a liquid sample is deposited into the pouch, the absorbent pad 80 preferably relatively thin (e.g., less than or equal to 5 mm thick, less than or equal to 4 mm thick, less than or equal to 3 mm thick, less than or equal to 2 mm thick, less than or equal to about 1 mm thick) and is configured to absorb a quantity of deionized water equal to many time its own weight (e.g., at least 100-times its own weight, at least 150-times its own weight, at least 200-times its own weight, at least 250-times its own weight, at least 300-times its own weight, at least 350-times its own weight, at least 400-times its own weight, at least 500-times its own weight). In any embodiment, the absorbent pad may comprise a plurality of materials such as, for example, a super-absorbent material (e.g., a superabsorbent polymer; "herein, "SAP") and a less-absorbent or nonabsorbent carrier (e.g., cellulosic fibers). A nonlimiting example of a suitable absorbent pad is a composite polyacrylate laminate structure comprising a superabsorbent polymer granule base disposed between two cellulose sheets. In any embodiment of the absorbent pad, the pad may comprise SAP granules disposed in an air-laid nonwoven material or SAP fibers blended with carrier fibers into a nonwoven material.

Optionally, in any embodiment (not shown), the absorbent pad may be coupled to a component of the pouch (e.g., the second wall portion) in the second compartment. Advantageously, this can keep the pad from deforming (e.g., as it swells with liquid migrating from the first compartment) to an extent that it loses contact with a substantial portion of the membrane filter. The pad may be coupled to the pouch via an adhesive (e.g., a pressure-sensitive adhesive), a thermal weld or other suitable attachment means known in the art. In any embodiment, the absorbent pad may be releasably coupled to the pouch (e.g., by a water-soluble gum). This embodiment hold the pad in a proper position to receive liquid passing through the membrane filter, but permits lateral movement of the pad as it swells due to absorption of a large quantity of the liquid.

In any embodiment, a device of the present disclosure further comprises an indicator reagent for indicating a presence of a viable microorganism. The indicator reagent is disposed in the pouch. In any embodiment, the indicator reagent may be disposed as a dry powder or dried coating in the first compartment and/or the second compartment of the pouch. In any embodiment, the indicator reagent can be disposed in an adhesive layer as described herein. Alternatively, or additionally, the indicator reagent may be a dry reagent coated onto an adhesive layer (e.g., with the cold water-soluble gelling agent as described herein).

In any embodiment, the indicator reagent may be a general indicator (e.g., a redox indicator such as triphenyltetrazolium chloride, for example) of viable microorganisms or an indicator of a large class of target microorganisms (e.g., total aerobic microorganisms). Alternatively, the indicator reagent can be an indicator (e.g., a chromogenic or fluorogenic enzyme substrate) that reacts with a smaller group of target microorganisms. A person having ordinary skill in the art will recognize an appropriate indicator reagent for a particular target microorganism.

In any embodiment of a device according to the present disclosure, the device further comprises a stand-off layer (not shown) disposed in the second compartment between the membrane filter and the absorbent pad. The stand-off layer is a relatively-thin (e.g., about 0.1 mm to 2 mm thick) sheet-like material. In any embodiment, the stand-off layer is shaped and dimensioned to be at least coextensive with the membrane filter. In any embodiment, the stand-off layer is substantially less absorbent than the absorbent pad. In any embodiment, the absorbency of the stand-off layer is less than or equal to the absorbency of the membrane filter. The stand-off layer may comprise or consist essentially of a hydrophobic material (e.g., unmodified polypropylene).

The stand-off layer functions to permit the passage of aqueous liquid from the membrane filter to the absorbent layer during the initial period in which over half of the aqueous liquid deposited into the first compartment passes into the second compartment, while restricting diffusion of nutrient from the first compartment to the second compartment while the device is being incubated to facilitate microbial colony growth.

Suitable materials for use as the stand-off layer include, for example nonwoven fabrics comprising polypropylene; polyethylene; polyethylene terephthalate; a blend of polyethylene terephthalate and cellulose; a blend of polyethylene terephthalate and rayon; and mixtures thereof. Advantageously, devices comprising the stand-off layer can include dry nutrients coated on the first wall portion of the pouch and can retain enough nutrients in the hydrated cold water-soluble gelling agent to support growth of the target microorganisms in the hydrated nutrient gel.

Figure 5:
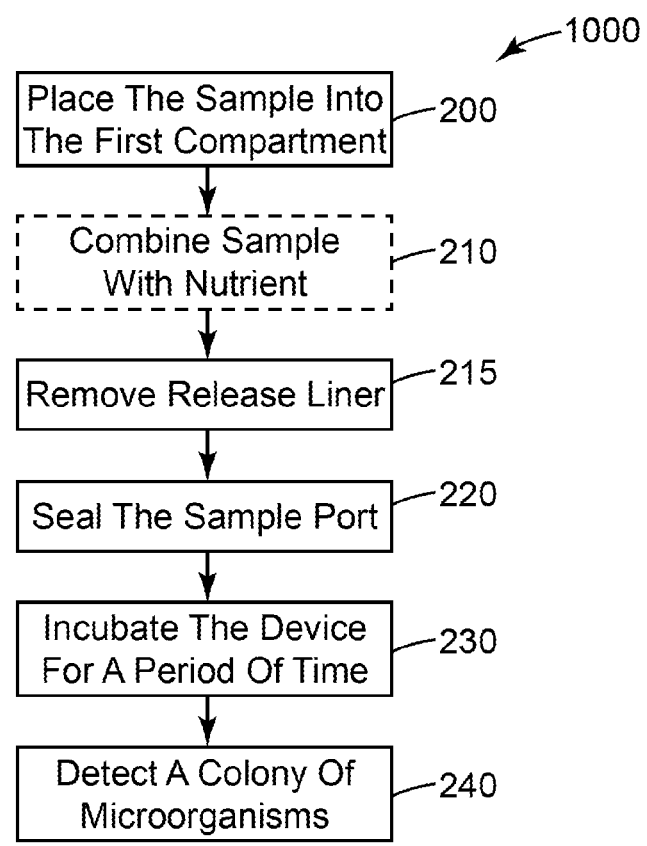
FIG. 5 is a block diagram of one embodiment of a method of detecting a target microorganism according to the present disclosure.

In another aspect, the present disclosure provides a method. The method can be used to detect and, optionally, enumerate target microorganisms in a liquid sample. FIG. 5 shows a block diagram that shows the steps of one embodiment of a method 1000 of detecting microorganisms in a liquid sample according to the present disclosure.

The method 1000 comprises a step 200 of placing a predetermined volume of aqueous sample into the first compartment of the device of any one of the embodiments of the present disclosure. The aqueous sample can be any filterable liquid sample to be tested for presence of a target microorganism. The method is particularly useful for water samples that are suspected of containing relatively low concentrations (e.g., less than or equal to 10 microorganisms per milliliter, less than or equal to 1 microorganism per milliliter, less than or equal to 0.1 microorganisms per milliliter, less than or equal to 0.01 microorganism per milliliter,) of target microorganisms. Placing a predetermined volume of aqueous sample into the first compartment of the device comprises placing the predetermined volume into the device (e.g., via pipetting, pouring, injecting, or the like) through the sealable sample port.

The method 1000 may further comprises a step 215 of removing the release liner 18 to expose the first adhesive layer 95 disposed on the second substrate 91. The method 1000 may further comprises a step 220 of sealing the device. Sealing the device may comprise contacting the first adhesive layer 95 with the first wall portion and contacting with the second adhesive layer 93 with the second wall portion to form a waterproof seal that closes the opening of the pouch.

In any embodiment of the method, air may be expelled (e.g., manually, by squeezing) from the pouch via the opening of the device before and or during the process of forming the waterproof seal.

The method 1000 further comprises a step 230 of incubating the device for a period of time at a temperature that facilitates growth and detection of a target microorganism. A person having ordinary skill in the art will recognize the incubation temperature and period of time will depend upon a number of factors (e.g., the target microorganism, nutrients present in the sample, nutrients present in the device, inhibitory agents present in the sample and/or the device) and will adjust the incubation time and temperature accordingly.

The method 1000 further comprises a step 240 of detecting a presence or an absence of a colony of the target microorganism in the device. In any embodiment, detecting a presence or an absence of a colony of the target microorganism in the device can comprise detecting a colony (e.g., visually or using machine vision) in the first compartment of the device. In any embodiment, detecting a presence or an absence of a colony of the target microorganism in the device can comprise detecting a change associated with the indicator reagent. The indicator reagent may change from a first state (e.g., substantially colorless or nonfluorescent) to a second state (e.g., colored or fluorescent) in and/or surrounding a colony of the target microorganism. In any embodiment, the colonies can be enumerated and, optionally, the number of colonies of target microorganisms can be recorded.

In any embodiment, after sealing the device, the method further comprises laying the outer surface of the first wall portion of the device or laying the outer surface of the second wall portion of the device onto a surface that is substantially perpendicular to gravitational force. Advantageously, laying the outer surface of its second wall portion of the device onto a surface that is substantially perpendicular to the force of gravity facilitates flow of the sample liquid through the membrane filter by force of gravity. In addition, laying the outer surface of its second wall portion of the device onto a surface that is substantially perpendicular to the force of gravity facilitates contact between the hydrated cold water-soluble gelling agent adhered to the first wall portion and the membrane filter as the liquid passes through the membrane filter from the first compartment to the second compartment.

In any embodiment, the method further comprises passing at least 90%, at least 92%, at least 95%, at least 97% or at least 98% of the predetermined volume from the first compartment to the second compartment. The portion of the predetermined volume that remains in the first compartment is substantially present as part of the gel formed by hydrating the cold water-soluble gelling agent.

In any embodiment, the method further comprises a step 210 of combining the aqueous sample with a nutrient, nutrient medium, indicator reagent and/or selective agent prior to placing the predetermined volume into the first compartment. In any embodiment, the method further comprises combining the aqueous sample with a nutrient, nutrient medium, indicator reagent and/or selective agent after placing the predetermined volume into the first compartment.

EXEMPLARY EMBODIMENTS

Embodiment 1 is a microbial detection device, comprising: a water-proof pouch comprising: a first wall portion having an inner surface and an outer surface; a second wall portion having an inner surface and an outer surface; a porous membrane filter disposed in the pouch between the inner surface of the first wall portion and the inner surface of the second wall portion, the membrane filter having a first major surface and a second major surface opposite the first major surface; a frame coupled to the membrane filter, the frame having a first major surface and a second major surface opposite the first major surface; a first compartment defined in part by inner surface of the first wall portion and defined in part by the first major surface of the membrane filter and the first major surface of the frame; a second compartment defined in part by the inner surface of the second wall portion and defined in part by the second major surface of the membrane filter and the second major surface of the frame; a dry cold water-soluble gelling agent in the first compartment; and an absorbent pad disposed in the second compartment; wherein the membrane filter permits passage of aqueous liquids from the first compartment to the second compartment and prevents passage of particles of a predetermined size from the first compartment to the second compartment; wherein the frame is coated on the first major surface with a first adhesive layer and on the second major surface with a second adhesive layer; wherein the frame comprises an aperture through which liquid passes from the first compartment into the membrane filter; a release liner removably adhered to the first adhesive layer, wherein part of the release liner faces the first wall portion.

Embodiment 2 is the device of embodiment 1, wherein the release liner is a I fold release liner.

Embodiment 3 is the device of any one of the preceding embodiments, wherein the release liner comprises a edge and at least a portion of the edge has a slope that is oriented at an effective angle α between 10 degrees and 80 degrees with respect to the longitudinal axis of the release liner.

Embodiment 4 is the device of embodiment 3, wherein effective angle α is about 45 degrees.

Embodiment 5 is the device of any one of the preceding embodiments, wherein the release liner comprises a tab for removal of the release liner from the microbial detection device.

Embodiment 6 is the device of any one of the preceding embodiments, wherein the pouch comprises a deformable first wall portion disposed opposite the membrane filter in the first compartment.

Embodiment 7 is the device of any one of the preceding embodiments, wherein the pouch comprises a deformable second wall portion disposed proximate the absorbent pad in the second compartment.

Embodiment 8 is the device of any one of the preceding embodiments, wherein the membrane filter comprises a supported membrane.

Embodiment 9 is the device of any one of the preceding embodiments, wherein the first wall portion or the second wall portion is fabricated from a sheet-like flexible film.

Embodiment 10 is the device of any one of the preceding embodiments, wherein the absorbent pad is coupled to the second wall portion or the absorbent pad is coupled to the frame.

Embodiment 11 is the device of any one of the preceding embodiments, wherein the first compartment has a first maximum capacity, wherein the device is dimensioned to receive a liquid sample having a volume between 25 mL and 150 mL, inclusive.

Embodiment 12 is the device of any one of the preceding embodiments, further comprising an indicator reagent for indicating a presence of a viable microorganism, wherein the indicator reagent is disposed in the pouch.

Embodiment 13 is a method comprising: placing a predetermined volume of aqueous sample into the first compartment of the device of any one of the preceding embodiments; removing the release liner; sealing the device; incubating the device for a period of time at a temperature that facilitates growth and detection of a target microorganism; and detecting a presence or an absence of a colony of the target microorganism in the device.

Embodiment 14 is the method of embodiment 13, further comprising laying the outer surface of the first wall portion of the device or laying the outer surface of the second wall portion of the device onto a surface that is substantially perpendicular to gravitational force.

Embodiment 15 is the method of any one of embodiments 13 through 14, further comprising passing at least 90% of the predetermined volume from the first compartment to the second compartment, wherein passing at least 90% of the predetermined volume comprises passing the volume by gravity force and/or capillary force.

Embodiment 16 is the method of any one of embodiments 13 through 15, further comprising the step of combining the aqueous sample with a nutrient, nutrient medium, indicator reagent and/or selective agent prior to placing the predetermined volume into the first compartment.

Embodiment 17 is the method of any one of embodiments 13 through 16, further comprising the step of combining the aqueous sample with a nutrient, nutrient medium, indicator reagent and/or selective agent after placing the predetermined volume into the first compartment.

Embodiment 18 is the method of any one of embodiments 13 through 17, further comprising counting microbial colonies in the device.

Advantages and embodiments of this disclosure are further illustrated by the following examples, but the particular materials and amounts thereof recited in these examples, as well as other conditions and details, should not be construed to unduly limit this disclosure. All materials are commercially available or known to those skilled in the art unless otherwise stated or apparent.

EXAMPLES

Example 1

Microbial detection devices were prepared according to FIG. 2. The second wall portion consisted of a 127 mm by 152.4 mm piece of clear BOPP film (1.6 mil (0.04 mm) thick and corona treated on both sides). The absorbent pad was a 101.6 mm by 127 mm piece of Gelok 30040-0305 superabsorbent polymer (SAP) laminate (300 g/m² of sodium polyacrylate granules laminated between tissue layers, Gelok Industries, Dunbridge, OH). The membrane filter was a 101.6 mm by 127 mm piece of DuraPES® 450 Membrane (5.5 mil (0.14 mm) thick hydrophilic polyethersulfone membrane for microfiltration obtained from the 3M Corporation, Maplewood, MN). A 101.6 mm by 127 mm piece of Fitesa-ADL2 non-woven material (Fitesa Company, Simpsonville, SC) was adhesively laminated between the SAP laminate and membrane using hot melt adhesive (#H4073A, Bostik Company, Milwaukee, WI). The resulting laminate was placed and centered on the inner surface of the second wall portion oriented such that the absorbent pad faced the inner surface of the second wall. In the orientation of this construction, a 12.7 mm strip along the perimeter of the inner surface of the second wall portion was not covered by the laminate.

A frame layer was prepared using 3M™ 1513 Transparent Polyester Double Sided Medical Tape (3M Company, Maplewood, MN). The double sided tape was subsequently cut to form a frame having external dimensions of 127 mm by 152.4 mm and a centered 76.2 mm by 101.6 mm internal opening. The resulting frame had a 25.4 mm wide adhesively coated border. The frame then was adhesively attached to the membrane filter and the inner surface of the second wall creating a partially constructed device that had a 76.2 mm by 101.6 mm section of the membrane uncovered on one side. A silicone coated paper release liner [1.25 inches (31.75 mm) wide] was attached along the entire length of one of the 127 mm edges on the exposed surface of the frame. Alternatively, a J-fold type silicone coated paper release liner (described in FIG. 4) with a tab (angle alpha of about 45 degrees) was attached along one of the 127 mm edges on the exposed surface of the frame.

A separate 76.2 mm wide by 101.6 mm long sheet of clear BOPP film (1.6 mil thick and corona treated on both sides) that had been coated on one side with an isooctyl acrylate/ acrylic acid (98/2 weight ratio) pressure-sensitive adhesive coating formulation containing TTC as described in Example 4 of U.S. Pat. No. 5,409,838 was powder coated with guar gum (Meyprogat 150, DuPont Corporation, Wilmington, DE). The powder was uniformly applied to the adhesive and excess powder was removed by hand shaking of the film. The powder coated film was then placed to cover the previously uncovered membrane of the partially constructed device. The film was oriented such that the coated side of the film faced the membrane. Double sided adhesive tape was applied to the perimeter of the side of the film opposite from the powder coating.

The first wall portion consisted of a 127 mm by 152.4 mm piece clear BOPP film (1.6 mil (0.04 mm) thick and corona treated on both sides). The first wall portion was then edge aligned with the frame section and adhesively attached to both the uncoated surface of the powder coated film (via the exposed adhesive surface of the double sided tape) and the exposed adhesive surface of the frame layer. This construction resulted in a pouch with an opening to a first compartment defined in part by the first wall portion and the membrane filter.

The complete disclosure of all patents, patent applications, and publications, and electronically available material cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims. All headings are for the convenience of the reader and should not be used to limit the meaning of the text that follows the heading, unless so specified. Various modifications may be made without departing from the spirit and scope of the invention. These and other embodiments are within the scope of the following claims.

The invention claimed is:

1. A microbial detection device, comprising:
 a water-proof pouch comprising:
  a first wall portion having an inner surface and an outer surface;
  a second wall portion having an inner surface and an outer surface;
 a porous membrane filter disposed in the pouch between the inner surface of the first wall portion and the inner surface of the second wall portion, the membrane filter having a first major surface and a second major surface opposite the first major surface;
 a frame coupled to the membrane filter, the frame having a first major surface and a second major surface opposite the first major surface;
 a first compartment defined in part by inner surface of the first wall portion and defined in part by the first major surface of the membrane filter and the first major surface of the frame;
 a second compartment defined in part by the inner surface of the second wall portion and defined in part by the second major surface of the membrane filter and the second major surface of the frame;
 a dry cold water-soluble gelling agent in the first compartment; and
 an absorbent pad disposed in the second compartment;
 wherein the membrane filter permits passage of aqueous liquids from the first compartment to the second compartment and prevents passage of particles of a predetermined size from the first compartment to the second compartment;
 wherein the frame is coated on the first major surface with a first adhesive layer and on the second major surface with a second adhesive layer;
 wherein the frame comprises an aperture through which liquid passes from the first compartment into the membrane filter;
 a release liner removably adhered to the first adhesive layer, wherein part of the release liner faces the first wall portion.

2. The device of claim 1, wherein the release liner is a J fold release liner.

3. The device of claim 1, wherein the release liner comprises a edge and at least a portion of the edge has a slope that is oriented at an effective angle α between 10 degrees and 80 degrees with respect to the longitudinal axis of the release liner.

4. The device of claim 3, wherein effective angle α is about 45 degrees.

5. The device of claim 1, wherein the release liner comprises a tab for removal of the release liner from the microbial detection device.

6. The device of claim 1, wherein the pouch comprises a deformable first wall portion disposed opposite the membrane filter in the first compartment.

7. The device of claim 1, wherein the pouch comprises a deformable second wall portion disposed proximate the absorbent pad in the second compartment.

8. The device of claim 1, wherein the membrane filter comprises a supported membrane.

9. The device of claim 1, wherein the first wall portion or the second wall portion is fabricated from a flexible film.

10. The device of claim 1, wherein the absorbent pad is coupled to the second wall portion or the absorbent pad is coupled to the frame.

11. The device of claim 1, wherein the first compartment has a first maximum capacity, wherein the device is dimensioned to receive a liquid sample having a volume between 25 mL and 150 mL, inclusive.

12. The device of claim 1, further comprising an indicator reagent for indicating a presence of a viable microorganism, wherein the indicator reagent is disposed in the pouch.

13. A method comprising:
placing a predetermined volume of aqueous sample into the first compartment of the device of claim 1;
removing the release liner;
sealing the device;
incubating the device for a period of time at a temperature that facilitates growth and detection of a target microorganism; and
detecting a presence or an absence of a colony of the target microorganism in the device.

14. The method of claim 13, further comprising laying the outer surface of the first wall portion of the device or laying the outer surface of the second wall portion of the device onto a surface that is substantially perpendicular to gravitational force.

15. The method of claim 13, further comprising passing at least 90% of the predetermined volume from the first compartment to the second compartment, wherein passing at least 90% of the predetermined volume comprises passing the volume by gravity force and/or capillary force.

16. The method of claim 13, further comprising the step of combining the aqueous sample with a nutrient, nutrient medium, indicator reagent and/or selective agent prior to placing the predetermined volume into the first compartment.

17. The method of claim 13, further comprising the step of combining the aqueous sample with a nutrient, nutrient medium, indicator reagent and/or selective agent after placing the predetermined volume into the first compartment.

18. The method of claim 13, further comprising counting microbial colonies in the device.

* * * * *